US008221742B2

(12) United States Patent
Rehberger et al.

(10) Patent No.: US 8,221,742 B2
(45) Date of Patent: Jul. 17, 2012

(54) **METHODS OF MAKING AND USING *LACTOBACILLUS* STRAINS**

(75) Inventors: Thomas G. Rehberger, Wauwatosa, WI (US); Charles V. Maxwell, Springdale, AR (US)

(73) Assignee: Agtech Products, Inc., Waukesha, WI (US)

(*) Notice: Subject to any disclaimer, the term of this patent is extended or adjusted under 35 U.S.C. 154(b) by 1137 days.

(21) Appl. No.: 12/055,136

(22) Filed: Mar. 25, 2008

(65) Prior Publication Data
US 2008/0171102 A1  Jul. 17, 2008

Related U.S. Application Data

(62) Division of application No. 10/624,443, filed on Jul. 22, 2003, now Pat. No. 7,354,757.

(60) Provisional application No. 60/397,654, filed on Jul. 22, 2002.

(51) Int. Cl.
*A01N 63/00* (2006.01)

(52) U.S. Cl. ............... 424/93.45; 435/252.9; 426/61; 426/2

(58) Field of Classification Search .................. None
See application file for complete search history.

(56) References Cited

U.S. PATENT DOCUMENTS

| | | | |
|---|---|---|---|
| 3,932,670 A | 1/1976 | Sakurai | |
| 3,984,575 A | 10/1976 | Farr | |
| 4,579,734 A | 4/1986 | Hata et al. | |
| 4,591,499 A | 5/1986 | Linn et al. | |
| 5,296,221 A | 3/1994 | Mitsuoka et al. | |
| 5,478,559 A | 12/1995 | Yabiki et al. | |
| 5,547,692 A | 8/1996 | Iritani et al. | |
| 5,705,152 A | 1/1998 | Plummer | |
| 5,725,853 A | 3/1998 | Dennis et al. | |
| 5,795,602 A | 8/1998 | Craig et al. | |
| 5,849,289 A | 12/1998 | Dobrogosz et al. | |
| 5,945,333 A | 8/1999 | Rehberger | |
| 6,060,050 A | 5/2000 | Brown et al. | |
| 6,090,416 A | 7/2000 | Iritani et al. | |
| 6,120,810 A | 9/2000 | Rehberger et al. | |
| 6,132,710 A | 10/2000 | Panigrahi et al. | |
| 6,221,650 B1 | 4/2001 | Rehberger | |
| 6,346,422 B1 | 2/2002 | Butty et al. | |
| 6,455,063 B1 | 9/2002 | Rehberger et al. | |
| 6,537,544 B1 | 3/2003 | Johansson et al. | |
| 2001/0031276 A1 | 10/2001 | Shelford et al. | |

FOREIGN PATENT DOCUMENTS

EP         0203586 A3    12/1986

OTHER PUBLICATIONS

Banach, S. et al, "Influence of *Lactobacillus brevis* 1E-1 on the gastrointestinal microflora of pre-weaning and weaning pigs," J. Animal Sci., V. 80, Supp 1/J. Dairy Sci., V. 85, Supp 1, p. 248 (abstract Jul. 21, 2002).

Benoit, V. et al, "Characterization of Brevicin 27, a bacteriocin synthetized by *Lactobacillus brevis* SB27," Current Microbiol. 28:53-61 (1994).
Brown, D. C. et al, "Effect of milk supplementation with *Lactobacillus brevis* 1E-1 on intestinal microflora, intestinal morphology and pig performance," J. Anim. Sci. 81(supp 2): p. 76 (2003).
Coventry, M. J. et al, "Production of Brevicin 286 by *Lactobacillus brevis* VB286 and partial characterization," J. Applied Bacteriology, 80:91-98 (1996).
Davis, M. E. et al, "Influence of *Lactobacillus brevis* 1E-1 on the gastrointestinal microflora, gut morphology, and pig performance pre- and post-weaning," 9th Intl Symposium on Digestive Physiology in Pigs, Banff, AG, Canada 2:265-267 (May 14-17, 2003).
Kraus, D. O. et al, "Ribotyping of Adherent *Lactobacillus* from weaning pigs: a basis for probiotic selection based on diet and gut compartment," Anaerobe 3:317-325 (1997).
Lewus, C. B. and Montville, T. J., "Detection of bacteriocins produced by lactic acid bacteria," J. Microbiological Methods 13:145-150 (1991).
Parrott, T. D. et al, "Characterization of the predominant *Lactobacilli* isolated form the gastrointestinal tract of post-weaned pigs," presented at the Am Soc for Microbiology Annual General Meeting, (May 23-27, 1994).
Schutz, H. et al, "Anaerobic reduction of glycerol to propanediol-1.3 by *Lactobacillus brevis* and *Lactobacillus buchneri*," System Appl Microbiol., 5:169-178 (1984).
Tannock, G. W. et al, "*Lactobacillus* succession in the piglet digestive tract demonstrated by plasmid profiling," Appl and Environmental Microbial, 56(5): 1310-1316 (May 1990).
EP Supplemental Search Report for related EP 03765947 (Feb. 22, 2006).
PCT International Search Report for related PCT/US03/22948 (Jul. 22, 2003).
Office Action mailed Jul. 7, 2006 for U.S. Appl. No. 10/624,443, filed Jul. 22, 2003.
Final Office Action mailed Feb. 22, 2007 for U.S. Appl. No. 10/624,443, filed Jul. 22, 2003.
EP Office Action mailed Feb. 3, 2011 for EP Application No. 03765947.1.
CA Office Action mailed Mar. 17, 2011 for CA Application 2,493,121.
Gebert, S., "*Lactobacillus brevis* strain 1E1 administered to piglets through milk supplementation prior to weaning maintains intestinal integrity after the weaning event", Beneficial Microbes, XXX 2011, Wageningen Academic Publishers.
Canadian Office Action mailed on Mar. 17, 2011 for Canadian Patent App. No. 2,493,121.
European Office Action mailed on Feb. 3, 2011 for European App. No. 03765947.1.

*Primary Examiner* — Irene Marx
(74) *Attorney, Agent, or Firm* — Whyte Hirschboeck Dudek S.C.; Michael J. Cronin

(57) ABSTRACT

*Lactobacillus* strains that have a genetic Profile I based on Apa I, Not I, and Xba I digests are provided. Preferably, the strains decrease level of at least one of coliforms and *E. coli* within the gastrointestinal tract of an animal. A direct-fed microbial that includes the strain is additionally provided. A method of feeding an animal the strain and a method of forming a direct fed microbial that includes the strain is also provided.

14 Claims, 10 Drawing Sheets

Figure 2. Mean coliform populations for pre-weaning pigs (9-13 days old).
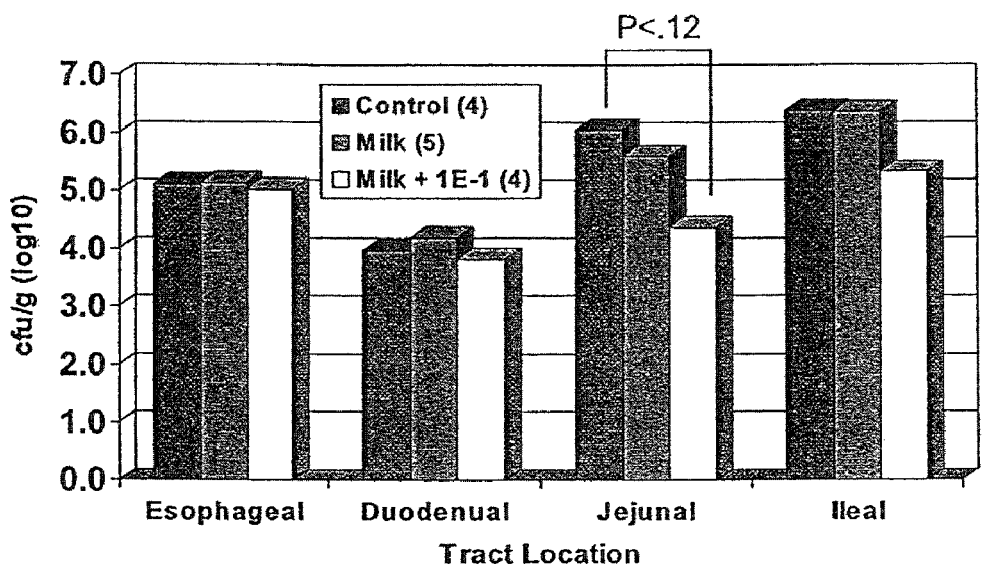
Figure 3. Mean E. coli populations for pre-weaning pigs (9-13 days old).
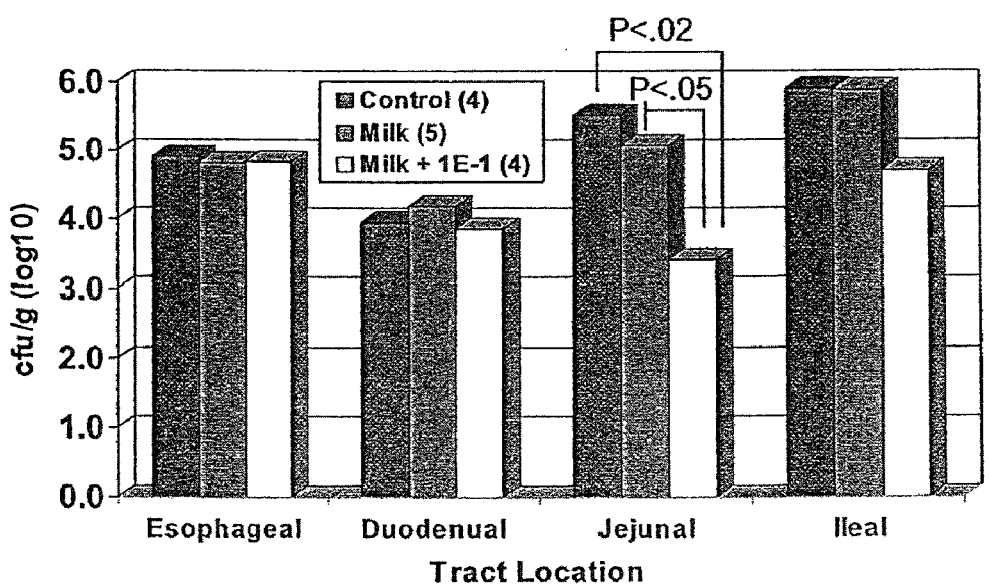

Figure 4. Mean coliform populations for weaning pigs (19-23 days old).
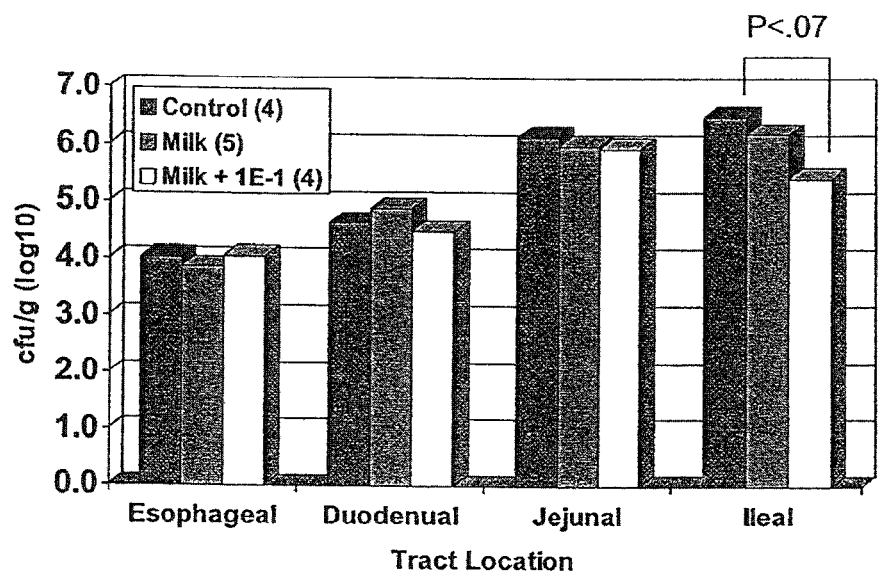
Figure 5. Mean E. coli populations for weaning pigs (19-23 days old).
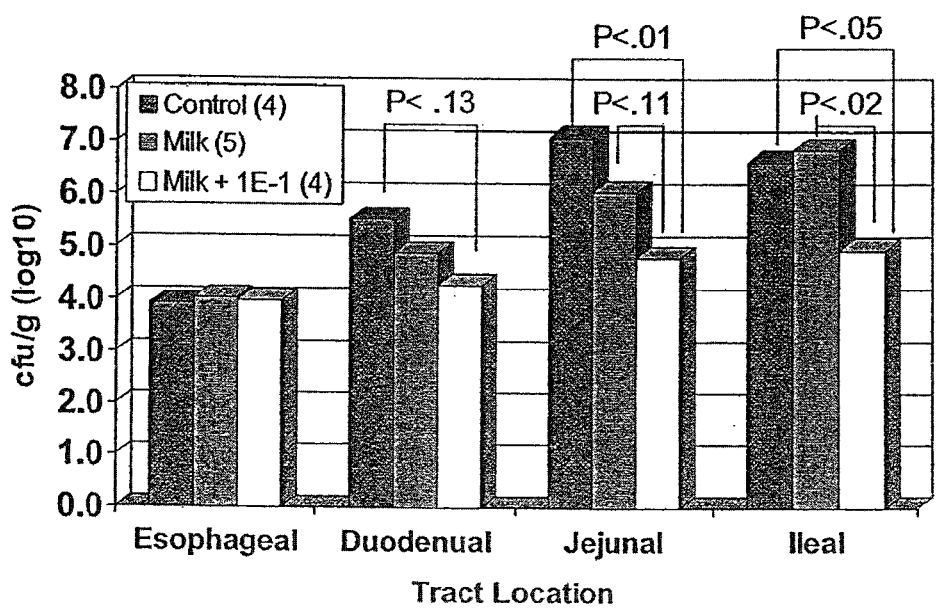

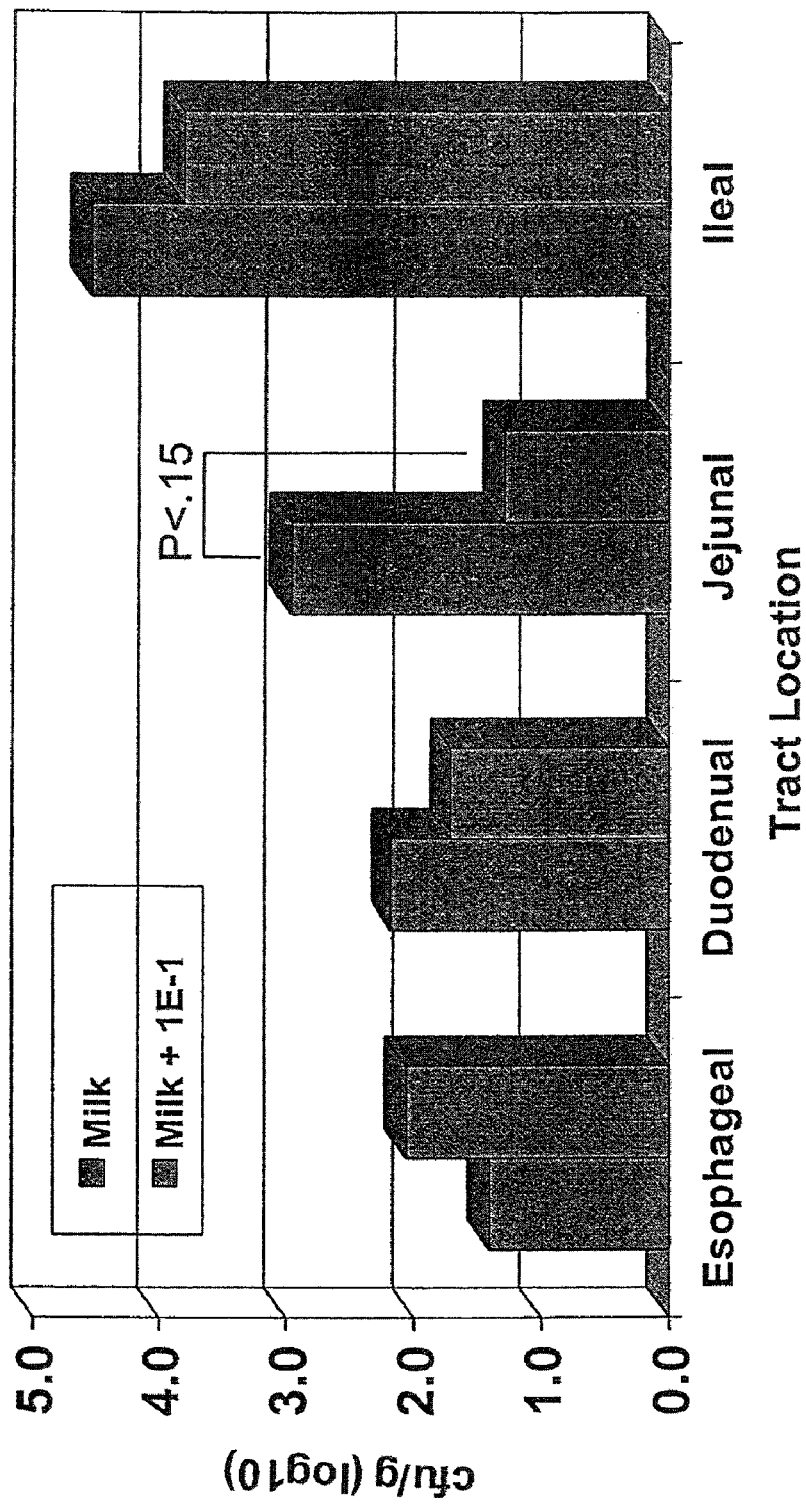
Figure 6. Mean coliform populations for pre-weaning pigs (10 days old).

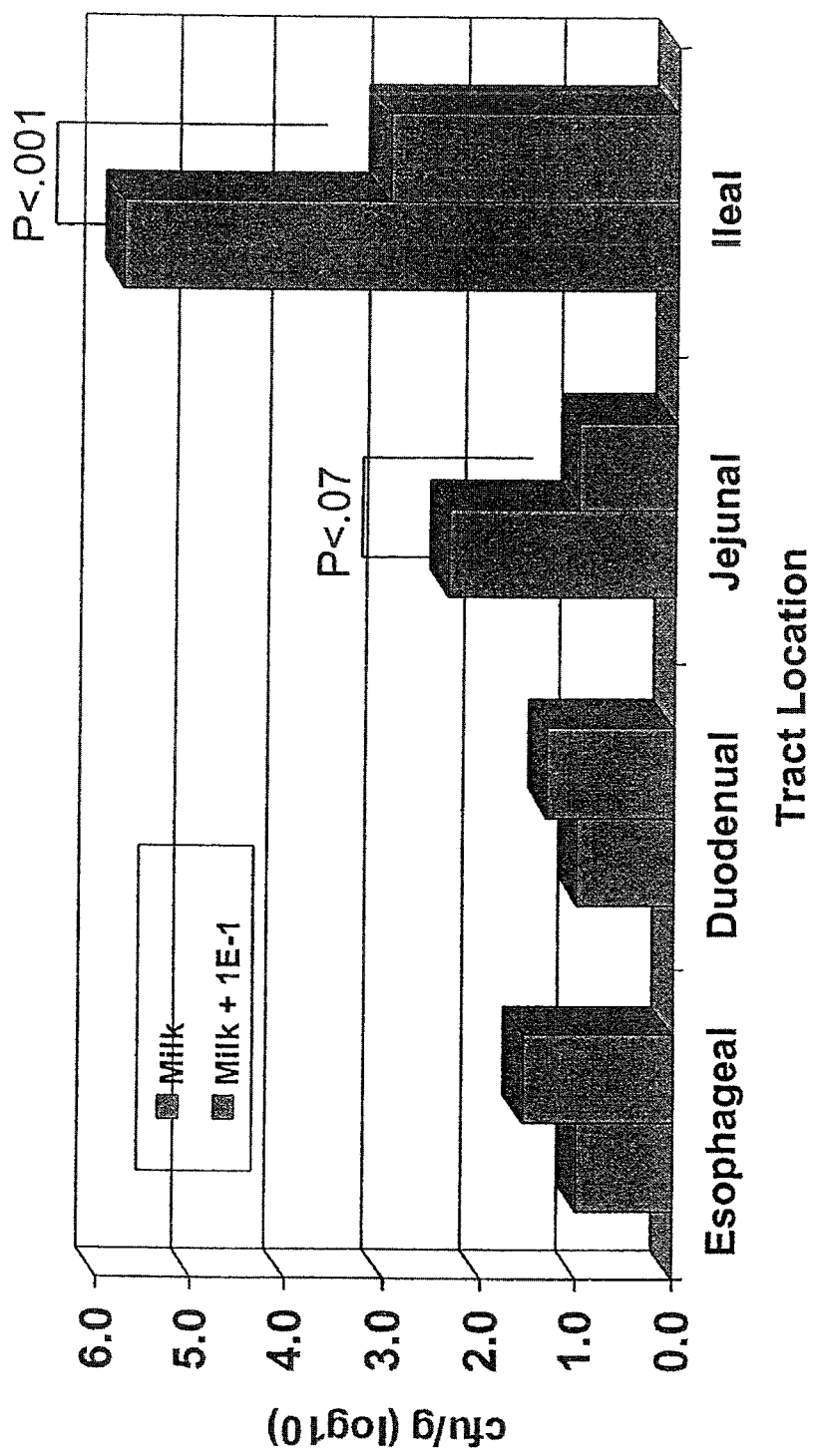
Figure 7. Mean coliform populations for weaning pigs (22 days old).

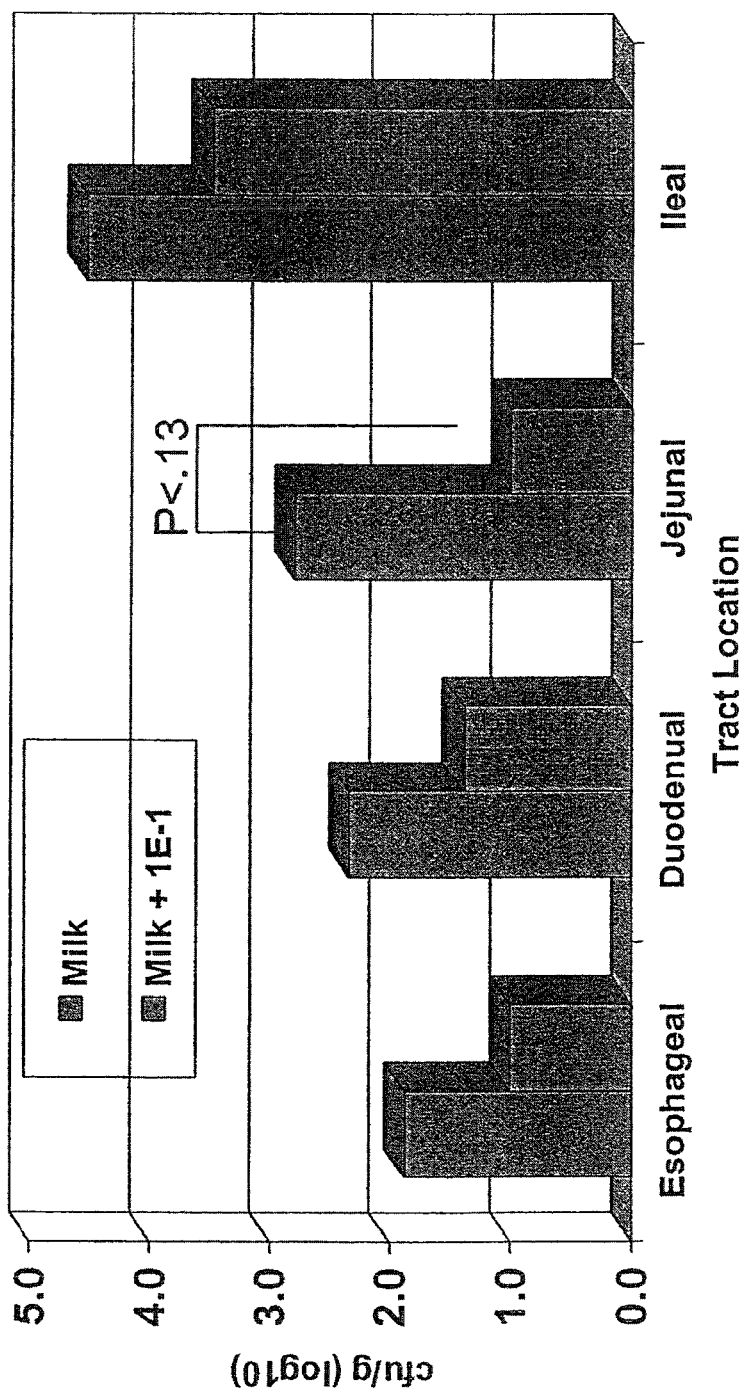
Figure 8. Mean *E. coli* populations for pre-weaning pigs (10 days old).

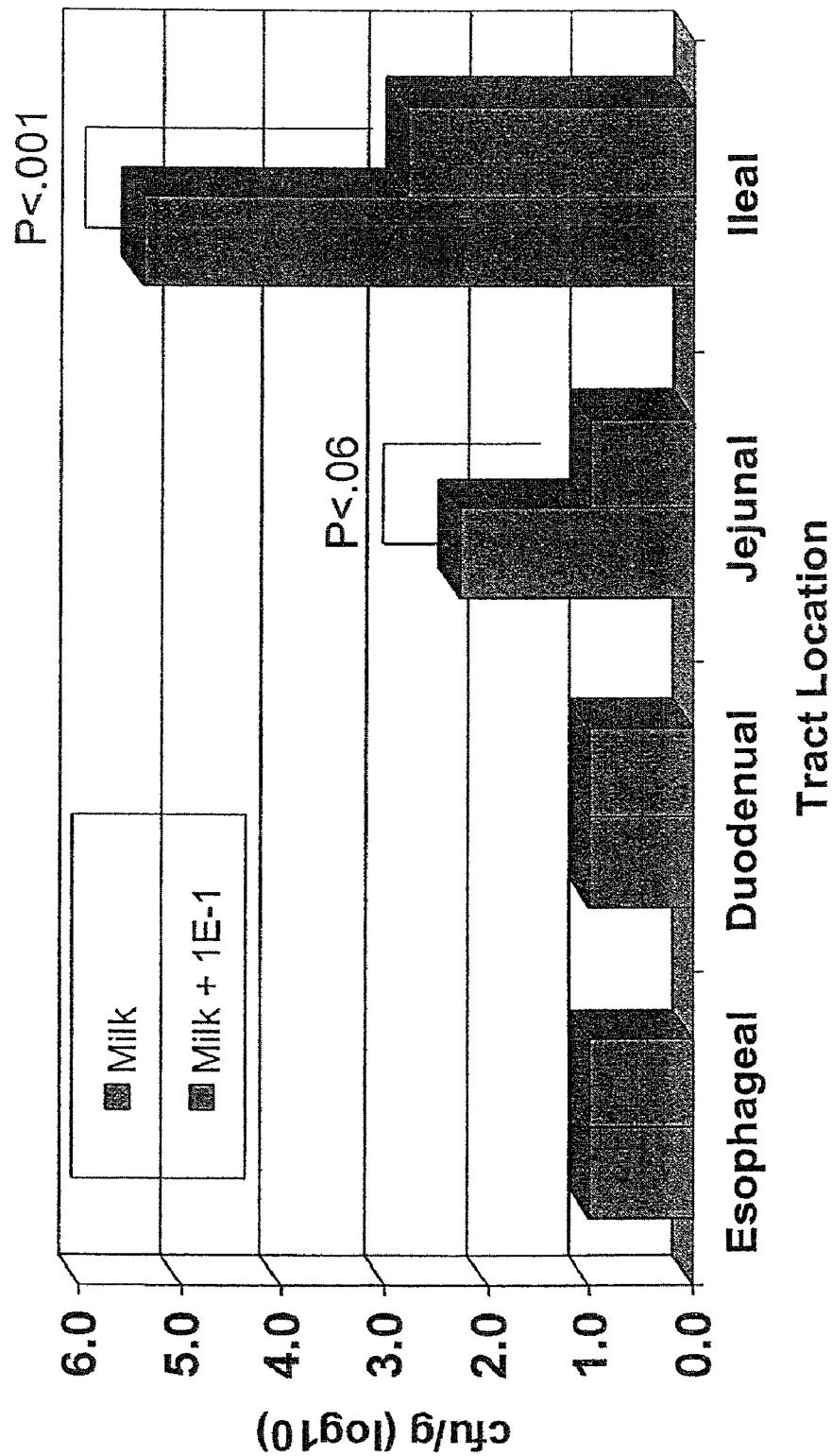

METHODS OF MAKING AND USING *LACTOBACILLUS* STRAINS

CROSS-REFERENCE TO RELATED APPLICATIONS

This application is a divisional of U.S. patent application Ser. No. 10/624,443, filed Jul. 22, 2003, which claims priority to U.S. Provisional Patent Application No. 60/397,654, filed Jul. 22, 2002, the entireties of both of which are incorporated by reference herein.

FIELD OF THE INVENTION

The invention relates to *Lactobacillus* strains for ingesting by animals. More particularly, though not exclusively, the present invention relates to *Lactobacillus* strains that are useful as direct-fed microbials for pigs.

BACKGROUND OF THE INVENTION

Strains of the genus *Lactobacillus* are normal inhabitants of the gastrointestinal tract of many animal species. In pigs, lactobacilli are one of the principal bacterial groups in the proximal region of the digestive tract (Barrow, P. A., R. Fuller, and N. J. Newport. 1977. Inft, Immun. 18: 586-595). Their beneficial role in the intestinal tract has been attributed to their ability to survive the digestive process, attach to the epithelial lining of the intestinal tract, produce lactic acid and other antimicrobial compounds, and prevent the colonization of pathogens via competitive exclusion (Savage, D. C. 1987. Factors affecting the biocontrol of bacterial pathogens in the intestine. Food Technol. 41: 82-87).

Many allogenic and autogenic factors influence the microbial population of the gastrointestinal tract (Savage, D. C. 1989. Rev. sci. tech Off. int. Epiz. 8: 259-273). Allogenic factors such as alterations in the diet and environment along with maturation of the host are major influences on the succession of *Lactobacillus* strains in the gastrointestinal tract of pigs during the post-weaning phase. Although it has been well documented that these changes may have severe effects on the host, little is understood about the distribution and diversity of lactobacilli species during this period.

Current industry practices to improve health and, more specifically, reduce the levels of coliforms and *E. coli* within the gastrointestinal tract of pigs generally include feeding antibiotics at subtherapeutic levels. However, the practice of feeding antibiotics to livestock has raised concerns about increasing the antibiotic resistance of microbial pathogens in the food supply.

Another approach to improving the health of animals is to alter the inhabitants of their gastrointestinal tract. Altering the inhabitants of the gastrointestinal tract of animals has been attempted by feeding direct-fed microbials to animals. The efficacy of single or multiple strains of *Lactobacillus* commonly used in commercial direct-fed microbials has been and continues to be debated. This debate is primarily due to inconsistent performance of previous direct-fed microbials. This inconsistency may be due to the fact that many commercial direct-fed microbials are composed of *Lactobacillus* strains commonly used as silage inoculants or cheese starter cultures. These strains may be effective to inoculate silage or to convert milk into cheese, but have no proven efficacy as direct fed microbials for animal feeding. While the "one strain for all products" approach may be an economical method for the commercial fermentation industry, this does not provide the best strains for each application.

In view of the foregoing, it would be desirable to provide a direct-fed microbial that reduces the levels of coliforms and *E. coli* within the gastrointestinal tract of pigs. In particular, it would be desirable to provide a direct-fed microbial that provides a healthier intestinal microflora during the weaning transition period in pigs.

SUMMARY OF THE INVENTION

The invention, which is defined by the claims set out at the end of this disclosure, is intended to solve at least some of the problems noted above. *Lactobacillus* strains that have a Profile I based on Apa I, Not I, and Xba I digests, as shown in FIG. 1 and Table 6, are provided. Preferably, the strains decrease levels of at least one of coliforms and *E. coli* within the gastrointestinal tract of an animal. Preferred strains include, but are not limited to *L. brevis* strains, *L. fermentum* strains, and *L. murinus* strains. Useful strains of the invention have been isolated from the pars oesophagea of a pig. A particularly preferred strain is *L. brevis* strain 1E-1, although any *Lactobacillus* strain having a Profile I based on Apa I, Not I, and Xba I digests, as shown in FIG. 1 and Table 6 are expected to work in the invention.

A method of feeding an animal is also provided. The method comprises feeding the animal a *Lactobacillus* strain that has a Profile I based on Apa I, Not I, and Xba I digests, as shown in FIG. 1 and Table 6. Preferably, the strain decreases levels of at least one of coliforms and *E. coli* within the gastrointestinal tract of an animal.

A direct-fed microbial is additionally provided. The direct-fed microbial includes at least one *Lactobacillus* strain that has a Profile I based on Apa I, Not I, and Xba I digests, as shown in FIG. 1 and Table 6. The direct-fed microbial additionally includes a carrier.

Also provided is a method of forming a direct fed microbial. In the method, a culture is grown in a liquid nutrient broth. The culture includes at least one *Lactobacillus* strain that has a Profile I based on Apa I, Not I, and Xba I digests, as shown in FIG. 1 and Table 6. The strain is separated from the liquid nutrient broth.

BRIEF DESCRIPTION OF THE DRAWINGS

Preferred exemplary embodiments of the invention are illustrated in the accompanying drawings.

FIG. 2 is a graph showing mean coliform for pre-weaning pigs 9-13 days old.

FIG. 3 is a graph showing mean *E. coli* for pre-weaning pigs 9-13 days old.

FIG. 4 is a graph showing mean coliform for weaning pigs 19-23 days old.

FIG. 5 is a graph showing mean *E. coli* for weaning pigs 19-23 days old.

FIG. 6 is graph showing mean coliform populations for pre-weaning pigs.

FIG. 7 is graph showing mean coliform populations for weaning pigs.

FIG. 8 is graph showing mean *E. coli* populations for pre-weaning pigs.

FIG. 9 is a graph showing mean *E. coli* populations for weaning pigs.

Figure 1:
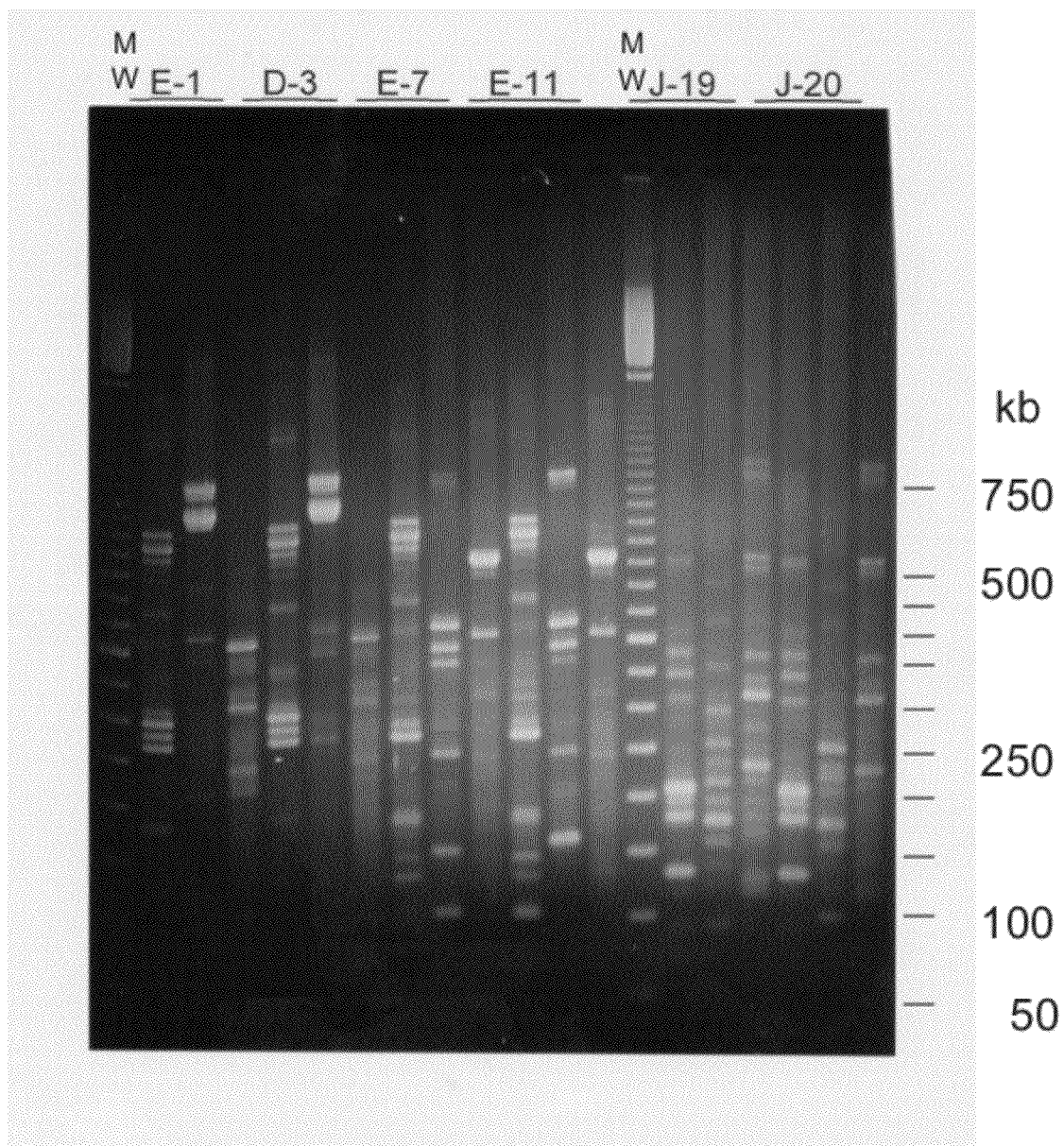
FIG. 1 shows Apa I, Not I, and Xba I digests of various strains from pig 1, including strain 1E-1.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

In accordance with the present invention, there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Described herein are *Lactobacillus* strains that have positive effects on the health of animals. Preferred *Lactobacillus* strains will now be described that are useful in pigs. This example is not intended to limit the invention to *Lactobacillus* strains usable only in pigs. The *Lactobacillus* strains of the invention are isolated from an animal, such as a pig. *Lactobacillus* strains of the invention preferably reduce the levels of coliforms and *E. coli* within the gastrointestinal tract of pigs. The *Lactobacillus* strains also provide a healthier intestinal microflora during a pre-weaning period in pigs. Thus, the *Lactobacillus* strains provide a healthier intestinal microflora during a pre-weaning and weaning period in pigs.

*Lactobacillus* strains of the invention have a profile I based on Apa I, Not I and Xba I digests, as shown in FIG. 1 and Table 6 (below). Preferred *Lactobacillus* strains include, but are not limited to, *L. brevis*, *L. fermentum*, and *L. murinus*. A preferred *Lactobacillus brevis* strain is 1E-1, which was isolated from the intestinal tract of a healthy, weaned pig. Strain 1E-1 is available from the microorganism collection of the American Type Culture Collection, 10801 University Blvd., Manassas, Va. 20110, under accession number PTA-6509, and was deposited on Jan. 12, 2005.

The *Lactobacillus* strains of the invention can be used as a direct-fed microbial. In a preferred embodiment, the direct-fed microbial is *L. brevis* strain 1E-1. Furthermore, the multiple *Lactobacillus* strains can be combined as a direct-fed microbial.

Characterization and Screening of *Lactobacillus* Strains:

In one exemplary evaluation of the bacteria of the present invention, the intestinal tracts of thirteen weaned pigs, ten healthy and three with scours, were sampled for the *Lactobacillus* strains found therein. As is detailed in Example 1 below, twenty-five numerically dominant isolates were selected from samples of the pars oesophagea, duodenum, jejunum, and ileum from each pig.

Isolates were identified using biochemical and carbohydrate fermentation tests. Plasmid profiling and pulsed-field gel electrophoresis (PFGE) were used to attempt to distinguish between strains of lactobacilli within a species. Higher numbers of lactobacilli were detected throughout the intestinal tract of healthy pigs when compared to the intestinal tract of sick pigs. The highest lactobacilli counts for both healthy and sick pigs were found in the pars oesophagea samples (healthy pigs-$1.3 \times 10^8$ CFU/g and sick pigs-$1.6 \times 10^6$ CFU/g). The lowest counts were found in the jejunal samples for both groups (healthy pigs-$1.9 \times 10^6$ CFU/g and sick pigs-$4.3 \times 10^5$ CFU/g).

Biochemical identification of the isolates indicated that the lactobacilli populations of healthy pigs were much more homogeneous than lactobacilli populations of sick pigs. In healthy pigs, the majority of the isolates were identified as *L. brevis*. Depending on the location, *L. brevis* accounted for 35-90% of the lactobacilli population. Similar, but not always, identical plasmid profiles were observed among *L. brevis* isolates. Identical plasmid profiles were observed among isolates identified as different species. PFGE was useful in identifying individual strains within a species.

Preparation and Feeding of *Lactobacillus* Strains:

A direct-fed microbial of the invention includes a *Lactobacillus* strain that has a Profile I based on Apa I, Not I and Xba I digests, as shown in FIG. 1 and Table 6. A preferred strain is the *L. brevis* strain 1E-1, although other *Lactobacillus* strains having a Profile I can be used. A carrier can be added to the direct-fed microbial. The carrier can be a liquid carrier, a solid carrier, or any other suitable carrier. A preferred liquid carrier is a milk replacer. Milk replacers are typically milk substitutes in powdered form that are mixed with water to form a composition that resembles milk. Another preferred liquid carrier is water. Dry carriers include, but are not limited to, animal feed.

The *Lactobacillus* strains of the present invention may be presented in various physical forms, for example, as a top dress, as a water soluble concentrate for use as a liquid drench or to be added to a milk replacer or gels. In a preferred embodiment of the top dress form of the *Lactobacillus* strains, a freeze-dried *Lactobacillus* strain fermentation product is added to a carrier, such as whey, limestone (calcium carbonate), rice hulls, yeast culture, dried starch, or sodium silico aluminate.

In a preferred embodiment of the water soluble concentrate for a liquid drench or milk replacer supplement, a freeze-dried *Lactobacillus* strain fermentation product is added to a water soluble carrier, such as whey, maltodextrin, sucrose, dextrose, dried starch, or sodium silico aluminate, and a liquid is added to form the drench or the supplement is added to milk or a milk replacer. In a preferred embodiment of the gels form, a *Lactobacillus* strain fermentation product is added to a carrier, such as one or more of vegetable oil, sucrose, silicon dioxide, polysorbate 80, propylene glycol, butylated hydroxyanisole, citric acid, and ethoxyquin to form the gel. An artificial coloring can be added to the gel.

Particularly preferred ways of feeding the direct-fed microbial include a milk supplement (replacer) fed during lactation 7-19 days prior to weaning, a single dose of a gel paste or drench given 1-2 days prior to weaning followed by dosing in water systems in the nursery for 7 days, and a single does of a gel paste or drench given 1-2 days prior to weaning followed by dosing in gruel feed in the nursery for 2-3 days. The direct-fed microbial can be fed in other forms, for differing periods of time, and at different stages in the pig's weaning.

Typically, the direct-fed microbial is formed by growing a culture including the *Lactobacillus* strain of choice in a liquid nutrient broth. The *Lactobacillus* strain of the culture is then separated from the liquid nutrient broth, such as by centrifugation. The *Lactobacillus* strain can then be freeze-dried. The freeze-dried *Lactobacillus* strain can be added to a carrier. This addition can be done immediately or at a subsequent time. Where the freeze-dried *Lactobacillus* strains are added at a subsequent time, they are preferably stored in a waterproof container, such as a foil pack.

The *Lactobacillus* strains of the invention can be fed to an animal. In a preferred embodiment, the animal is fed a *Lactobacillus brevis* strain 1-E1. Particularly useful results have been obtained when young pigs, including pre-weaning pigs, weaned pigs, and post-weaned pigs, are fed one or more the *Lactobacillus* strain of the invention.

Preferably, the animal is fed the *Lactobacillus* strain such that the amount of *Lactobacillus* strain delivered to the animal is about $1\times10^8$ CFU to about $1\times10^{10}$ CFU per day. More preferably, the animal is fed the *Lactobacillus* strain such that the amount of *Lactobacillus* strain delivered to the animal is about $5\times10^9$ CFU per day. However, it should be noted that higher and lower doses of the *Lactobacillus* strain can be fed to the animal and are believed to have a positive effect on the animal.

As is shown below in detail, feeding the *Lactobacillus* strain of the invention to animals altered the intestinal flora of the animals, decreasing levels of coliforms and *E. coli* in the animals. Maintaining a normal healthy intestinal microflora during the profound environmental and nutritional changes at weaning is critical to ensure optimal performance for pigs. Feeding the *Lactobacillus* strain of the invention also increased the average daily gain, increased the villus:crypt ratio in the animals, and decreased the number of sulfuric goblet cells, as is also shown in detail below.

Effect of Feeding *Lactobacillus* Strain 1E-1 on Pre-Weaning and Post-Weaning Pigs:

The effects of feeding *L. brevis* strain 1E-1 on the gastrointestinal microflora of pre-weaning, weaning, and post-weaning pigs have been determined. As is detailed below in Example 2, sows and gilts were randomly assigned to one of three treatments. In Example 2, four litters received no milk replacer (control), five litters received milk replacer, and five litters received milk replacer supplemented with strain 1E-1.

In Example 2, coliforms and *E. coli* were enumerated from pars oesophageal, duodenal, jejunal, and ileal regions of intestinal tracts from one pig per litter at 9-13 days of age (pre-weaning) and at 19-23 days of age (weaning). In pre-weaning pigs, *E. coli* and coliform populations in pars oesophageal, duodenal, and ileal regions of pre-weaning pigs were not significantly different in the three groups. As is shown in more detail in Example 2, pigs receiving strain 1E-1 had significantly lower jejunal *E. coli* populations compared to control (P<0.02) and milk replacer (P<0.05). Jejunal coliform populations tended to be lower for pigs receiving strain 1E-1 compared to control pigs (P<0.12) but were not significantly different compared to pigs receiving milk replacer. There were no treatment effects on populations of coliforms and *E. coli* in the pars oesophageal and duodenal regions for pigs at weaning. Pigs receiving strain 1E-1 had significantly lower *E. coli* populations in the jejunal region compared to control (P<0.01) and milk replacer (P<0.11). There were no significant treatment effects on jejunal coliform populations for pigs at weaning. In the ileal region of weaning pigs, the coliform populations neared significance for pigs receiving strain 1E-1 when compared to control (P<0.07). *E. coli* populations were significantly lower for pigs receiving strain 1E-1 compared to control pigs (P<0.05) and pigs receiving milk replacer (P<0.02). These results show that feeding strain 1E-1 provides a healthier intestinal microflora during lactation.

The use of *L. brevis* strain 1E-1 is shown herein to reduce the levels of coliforms and *E. coli* within the gastrointestinal tract of pigs, providing a healthier intestinal microflora during the pre-weaning period. The strongest response shown by strain 1E-1 was in the distal regions of the gastrointestinal tract more than the proximal regions, within pigs at weaning (19-23 days old) more than the pre-weaning pigs (9-13 days old), and against *E. coli* more than coliforms.

In addition, feeding the *Lactobacillus* strain to animals improves the health of the animal. For instance, feeding the *Lactobacillus* strain to young pigs decreases the incidence of scours in the young pigs.

Additionally, as is detailed below in Example 3, populations of *E. coli* and coliforms in the small intestine were reduced pre- and post-weaning when pigs were supplemented with 1E-1.

Intestinal morphology improved when animals were fed the *Lactobacillus* strain of the invention. For instance, villus: crypt ratio was greater and the number of sulfuric goblet cells was less with supplementation with the *Lactobacillus* strain. These data indicate that supplementing with strain 1E-1 and other strains having a Profile I based on Apa I, Not I and Xba I digests, as shown in FIG. 1 and Table 6 pre-weaning improves nursery performance and provides a healthier intestinal environment. An increase in weight at weaning in pigs fed the *Lactobacillus* strain was also observed.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Characterization of the Predominant Lactobacilli Isolated from the Intestinal Tract of Post-Weaned Pigs Materials and Methods Pigs: Thirteen crossbred pigs raised in a commercial facility in Arkansas were used in this study. After weaning at 21 days, pigs were fed a complex Phase 1 prestarter diet. At 7-10 days post-weaning, 3-5 pigs were selected from either a healthy group or a group of pigs identified as having scours and transported to Oklahoma State University. Pigs were killed by exsanguation and samples of the pars oesophagea, duodenum, jejunum, and ileum were aseptically removed along with 25 g samples of fecal and stomach contents. Three repetitions of this procedure were completed for a total sample size of 13 pigs (10 healthy and 3 with scours).

Isolation and maintenance of cultures: Pars oesophagea, duodenal, jejunal, and ileal sections were washed with 20 ml of sterile buffer (0.3 mM $KH_2PO_4$, 1 mM $MgSO_4$, 0.05% cysteine hydrochloride, pH 7.0) and cut open with surgical scissors to expose the epithelial lining. To remove cells from intestinal tissue, 22 g samples were placed in sterile bags and agitated in a stomacher for 60 sec. Stomach and fecal contents were suspended in sterile buffer and mixed by stomaching. Lactobacilli populations were enumerated on LBS agar. Plates were incubated anaerobically (GasPak) for 48 h at 37° C. Twenty-five isolated colonies from the highest dilution of each tissue sample were picked into 10 ml tubes of MRS (Difco, Detroit, Mich.) broth. Strains were routinely propagated in MRS broth (Difco, Detroit, Mich.) at 37° C. and stored in MRS broth containing 10% glycerol at −75° C.

Biochemical screening of isolates: Isolates picked from LBS plates were confirmed as lactobacilli by the Gram-stain reaction, cell morphology, and catalase reaction. The species identity of isolates was determined using API Rapid CH kits (Analytab Products, Plainview, N.Y.) according to the manufacturer's directions. Fermentation patterns were observed and recorded for each isolate at 24, 36, and 48 h. Fermentation patterns of each isolate were compared to differential characteristics provided in Bergey's Manual for species identification.

Plasmid DNA Isolation: Plasmid DNA was isolated from the lactobacilli strains as follows: a 1% inoculum taken from a 24 hour culture was placed into 10 ml of sterile MRS broth and incubated at 37° C. until the optical density (660 nm) reached 0.8 (log phase). Cell suspensions were then harvested by centrifugation (12,000×g for 15 min). The supernatant was decanted and the pellet resuspended in 1 ml of Tris-EDTA buffer containing 15% sucrose. Resuspended cells were stored in 1.5 ml centrifuge tubes at −20° C. until plasmid DNA analysis was performed. Frozen samples were allowed to thaw at room temperature. Cells were washed by harvesting (12,000×g for 5 minutes) and resuspending the pellet in 1 ml of Tris-EDTA buffer containing 15% sucrose. After washing, the pellet was resuspended to a final volume of 250 µl with fresh Tris-EDTA-sucrose buffer and mixed well by vortexing. Lysozyme (50 µl of a 60 mg/ml solution) was added, and the tubes were incubated on ice for 1 hour. Pronase (10 mg/ml: pre-incubated at 37° C. for 1 hour) was added (35 µl) followed by incubation at 37° C. for 30 minutes.

Following incubation, 0.25 M EDTA was added (111 µl) to the sample and the tubes held for 15 minutes on ice. Tris-EDTA containing 20% SDS was added (111 µl) and held on ice for an additional 15 minutes. Sodium acetate (75 µl of a 3.0 M solution) was added followed by a 30 minute incubation on ice. Debris was pelleted by centrifugation (12,000×g for 15 minutes) and the supernatant transferred to a clean 1.5 ml microcentrifuge tube. Cold ethanol (750 µl of 95%) was added to the tube containing the supernatant and mixed well by gently inverting the tube several times. The samples were stored at −20° C. for 1 hour to precipitate the DNA. DNA was pelleted by centrifugation (12,000×g for 15 minutes) and allowed to dry. The DNA was resuspended in 40 µl Tris-EDTA buffer, 5 µl of tracking dye was added and the mixture loaded onto an agarose gel. DNA was separated by gel electrophoresis using a 0.7% agarose gel at 50 volts. Agarose gels were examined after a 45 minute staining period in ethidium bromide solution.

Preparation of Intact Genomic DNA: Intact Genomic DNA from Representative strains was isolated from cells embedded in agarose beads using a modification of the method of Rehberger, T. G. 1993. Curr. Microbiol. 27: 21-25. Cultures were grown to mid-log stage in MRS broth, harvested by centrifugation (9,000×g for 10 min), and resuspended to one-tenth the original volume in ET buffer (50 mM EDTA, 1 mM Tris-HCl, pH 8.0). The cell suspension was mixed with an equal volume of 1% low-melting point agarose (Beckman Instruments, Palo Alto, Calif.), loaded into a syringe and injected into tygon tubing where it was allowed to solidify. The solidified cell-agarose mixture was forced into cold ET buffer and gently vortexed to break the string into smaller bead like pieces. The beads were resuspended in 10 ml of 10×ET buffer containing 5 mg/ml of lysozyme and incubated on ice for 2 hours to digest the cell wall material.

After incubation, the beads were harvested by centrifugation (4,000×g for 10 min) and resuspended in 10 ml of lysis buffer (10×ET buffer containing 100 ug/ml of proteinase K and 1% Sarkosyl), followed by incubation at 55 C for 5-7 hours to lyse the cells and release the genomic DNA. After cellular lysis, the beads were harvested by centrifugation (4,000×g for 10 min), resuspended in 10 ml of 1 mM phenyl-methylsulfonyl fluoride, and incubated at room temperature for 2 hours to remove contaminating protease activity. The beads containing the purified DNA were washed three times in TE buffer (10 mM Tris-HCl, 1 mM EDTA-Na$_2$, pH 7.5), resuspended in 10 ml of TE buffer and stored at 4° C. until restriction endonuclease digestion.

In situ restriction endonuclease digestion and pulsed gel electrophoresis: Agarose beads containing DNA were equilibrated in 1× restriction endonuclease buffer for 1 hour before enzyme digestion. After the beads were equilibrated, 10-20 units of the restriction enzyme were added to 90 ul of beads and incubated at the appropriate temperature for 6-8 hours. Following digestion, the enzymes were inactivated by heating for 10 minutes at 65° C. This melted the beads and allowed for easy loading onto the gel for fragment separation.

DNA fragments were separated on 1.0% agarose gels in 0.5×TBE buffer at 15° C. for 20 hours using a CHEF-DRIII electrophoresis system (Bio-Rad, Hercules, Calif.). Each set of restriction endonuclease digests were separated at different initial and final pulse times to provide maximum separation of small, medium, and large fragments. To determine the molecular size of the DNA fragments lambda DNA multimers, intact yeast chromosomes and restriction fragments of lambda DNA were included as standards.

Results and Discussion

Higher mean numbers of lactobacilli populations were detected in all gastrointestinal samples from healthy pigs compared to pigs with scours (Table 1). However, the variation in the lactobacilli populations among healthy pigs for all sample locations was greater than the difference seen between healthy and sick pigs.

TABLE 1

Populations of *lactobacilli* in the digestive tract of post-weaning pigs.

| Pig Number | *Lactobacillus* populations[a] Location[b] | | | | | |
|---|---|---|---|---|---|---|
| | E | D | J | I | S | F |
| Healthy | | | | | | |
| 1 | 6.61 | 4.64 | 3.82 | 4.08 | 5.69 | 8.86 |
| 2 | 6.04 | 5.44 | 4.72 | 3.90 | 6.08 | 5.20 |
| 3 | 7.76 | 5.83 | 6.44 | 5.67 | 8.63 | 9.30 |
| 4 | 8.23 | 5.52 | 6.86 | 6.46 | 7.67 | 9.74 |
| 5 | 8.73 | 7.72 | 6.11 | 6.63 | 8.98 | 9.97 |
| 6 | 7.14 | 5.08 | 5.89 | 6.18 | 8.14 | 9.28 |
| 7 | 8.58 | 6.34 | 6.63 | 8.52 | 8.26 | 8.61 |
| 8 | 7.99 | 5.72 | 5.50 | 5.20 | 8.04 | 9.50 |
| 9 | 6.99 | 5.94 | 6.18 | 7.20 | 7.50 | 8.72 |
| 10 | 7.41 | 5.66 | 6.08 | 5.59 | 8.44 | 9.65 |
| Scour | | | | | | |
| 13 | 5.98 | 4.93 | 4.08 | 4.04 | 6.96 | 4.81 |
| 14 | 6.41 | 6.88 | 6.00 | 6.64 | 7.26 | 9.20 |
| 15 | 6.08 | 4.99 | 5.44 | 5.62 | 6.64 | 7.80 |

[a]Log10 *lactobacilli* per ml or g of sample.
[b]Symbols: E = pars oesophagea, D = duodenum, J = jejunum, I = ileum, S = stomach contents, F = feces.

Independent of the health of the animal, differences in lactobacilli populations were observed among different regions in the gastrointestinal tract. The par oesophageal region of all animals contained the highest number of lactobacilli compared to other gastrointestinal regions. The jejunal region of all animals contained the lowest number of lactobacilli compared to other gastrointestinal regions.

Identification of the predominant *Lactobacillus* species from the digestive tract samples is shown in Table 2. In some cases, the predominant species accounted for 100% of the total lactobacilli population. *L. brevis* and *L. murinus* were found to be the most common predominant species in healthy pigs while *L. plantarum* and *L. murinus* were found to be most common in pigs with scours.

TABLE 2

Identification of the predominant *Lactobacillus* species from digestive tract samples of representative pigs.

| Pig Number | Location[a] | Major species[b] | Percentage[c] |
|---|---|---|---|
| Healthy | | | |
| 1 | E | L. brevis | 57 |
| | D | L. brevis | 95 |
| | J | L. brevis | 50 |
| | I | L. brevis | 100 |
| 2 | E | L. brevis | 40 |
| | D | L. brevis | 100 |
| | J | L. brevis | 80 |
| | I | L. brevis | 60 |
| 3 | E | L. murinus | 63 |
| | D | L. murinus | 80 |
| | J | L. fermentum | 30 |
| | I | L. murinus | 44 |
| 7 | E | L. murinus | 80 |
| | D | various strains | 50 |
| | J | L. brevis | 82 |
| | I | L. acidophilus | 59 |
| 10 | E | L. plantarum | 50 |
| | D | L. murinus | 70 |
| | J | L. murinus | 90 |
| | I | L. murinus | 60 |
| Scour | | | |
| 13 | E | L. plantarum | 56 |
| | D | L. plantarum | 64 |
| | J | L. plantarum | 70 |
| | I | L. murinus | 60 |
| 14 | E | L. fermentum | 60 |
| | D | L. brevis | 32 |
| | J | L. murinus | 80 |
| | I | L. murinus | 56 |

[a]Symbols: E = pars oesophagea, D = duodenum, J = jejunum, I = ileum
[b]as determined by carbohydrate fermentation patterns
[c]ercent of the total lactobacilli from each location for each pig The predominant *Lactobacillus* species identified for each region of the digestive tract (Table 3) was found to be different between healthy and sick pigs. *L. brevis* was found to be the most common predominant species in three regions of healthy pigs while *L. plantarum* and *L. murinus* were found to be most common in two regions each of pigs with scours.

TABLE 3

Predominant *Lactobacillus* species isolated from different regions of the digestive tract.

| Health Status | Location[a] | Major species[b] | Percentage[c] |
|---|---|---|---|
| Healthy | E | L. brevis | 39 |
| | | L. murinus | 44 |
| | D | L. brevis | 52 |
| | | L. murinus | 35 |
| | J | L. brevis | 45 |
| | I | L. brevis | 43 |
| Scour | E | L. plantarum | 26 |
| | | L. fermentum | 30 |
| | D | L. plantarum | 32 |
| | J | L. murinus | 55 |
| | | L. plantarum | 35 |
| | I | L. murinus | 55 |
| | | L. plantarum | 40 |

[a]Symbols: E = pars oesophagea, D = duodenum, J = jejunum, I = ileum
[b]as determined by carbohydrate fermentation patterns
[c]mean percentage of total lactobacilli from all pigs The predominant *Lactobacillus* species identified from each pig examined (Table 4) indicated that *L. brevis* was the predominant species in 3 of the 5 healthy pigs and *L. plantarum* and *L. murinus* were the predominant species in pigs with scours.

TABLE 4

Predominant *Lactobacillus* species isolated from representative pigs.

| Pig Number | Major species[a] | Percentage[b] |
|---|---|---|
| Healthy | | |
| 1 | L. brevis | 76 |
| 2 | L. brevis | 69 |
| 3 | L. murinus | 49 |
| 7 | L. brevis | 37 |
| 10 | L. murinus | 60 |
| Scour | | |
| 13 | L. plantarum | 59 |
| 14 | L. murinus | 30 |

[a]as determined by carbohydrate fermentation patterns
[b]mean percentage of total *lactobacilli* from all locations Plasmid profiling was used in an attempt to distinguish strains of lactobacilli. Strains were assigned to a plasmid profile type for comparison to other strains from different regions and pigs. Table 5 lists the seven major profile types observed in this study. All plasmid profiles types were found to be common to two or more pigs and two or more regions. However, no profile type was shared among healthy and sick pigs. Fewer number of isolates were examined (140) for plasmids from sick pigs, which may have affected this observation. Plasmid profile type I was the most common profile in healthy pigs, while type III was most common in pigs with scours. Plasmid profiling was not as discriminatory a typing technique as genomic DNA fingerprinting to distinguish between strains within a species.

TABLE 5

Identification of the predominant plasmid profiles.

| Plasmid Profile | Number of Plasmids | Molecular weights (kb) | Examples |
|---|---|---|---|
| I | 7 | 2.5, 2.7, 3.1, 13.6, 71.5 | 2D-4, 7J-3, 10J-8 |
| II | 6 | 3.2, 6.2, 7.4, 32.1 | 2D-8, 2D-17, 7J-6 |
| III | 2 | 3.4, 3.7 | 13I-2, 13J-8, 13D-16 |
| IV | 3 | 3.9, 14.2 | 14J-1, 14J-4, 14J-7 |
| V | 4 | 2.5, 3.5, 4.2, 22.6 | 7E-2, 7E-4, 7E-6 |
| VI | 4 | 3.5, 4.5, 20.2 | 7E-8, 7E-9, 7E-10 |
| VII | 0 | | N/A |

N/A no example of profile

Comparisons of genomic DNA fingerprints produced by restriction endonuclease digestion of intact genomic DNA were used to determine the genetic relatedness among strains (data not shown). In general, a majority of strains isolated from the same animal were found to have identical Apa I, Not I, and Xba I fingerprints. Populations of lactobacilli in different gastric regions were composed of similar strains. To date, no evidence was found indicating distinct populations for the different regions of the gastrointestinal tract examined in this study. In contrast, distinct populations were identified that were specific for healthy and sick pigs. These findings indicate a distinct difference in the dominant strains of the lactobacilli populations between healthy and sick pigs.

Pulsed-field gel electrophoresis was useful at identifying differences among phenotypically indistinguishable strains. As an example, at least three different L. brevis strains and three different L. murinus have been identified from the isolates examined from pig 1 (Table 6). In addition, genomic fingerprints have also been found to be identical between phenotypically different strains. This may be due to genetic changes in the genes responsible for the carbohydrate fermentation(s) found to distinguish the strains biochemically. These changes could have resulted in the loss of function but may not have altered the restriction sites or the distances between them and therefore, go undetected as differences by genomic fingerprints.

TABLE 6

Genomic restriction endonuclease digestion profiles of lactobacilli from representative pigs

| | Genomic digestion profile[a] | Strain | Biochemical identification |
|---|---|---|---|
| Pig 1 | I | E-1 | L. brevis |
| | | D-3 | L. fermentum |
| | | D-5 | L. brevis |
| | | D-15 | L. brevis |
| | | D-22 | L. brevis |
| | | J-3 | L. brevis |
| | | J-6 | L. murinus |
| | | J-8 | L. murinus |
| | | I-5 | L. brevis |
| | | I-14 | L. brevis |
| | | I-17 | L. brevis |
| | | I-24 | L brevis |
| | II | E-7 | L. brevis |
| | | E-11 | L. murinus |
| | | E-17 | L. brevis |
| | | E-25 | L. brevis |
| | III | J-19 | L. murinus |
| | | J-20 | NA |
| | IV | E-23 | L. brevis |
| Pig 13 | V | E-1 | NA |
| | | E-2 | L. plantarum |
| | | E-3 | L. murinus |
| | | E-6 | L. agilis |
| | | E-8 | L. plantarum |
| | | D-1 | L. plantarum |
| | | D-2 | L. plantarum |
| | | D-3 | L. agilis |
| | | D-7 | L. agilis |
| | | J-1 | L. plantarum |
| | | J-3 | L. murinus |
| | | J-4 | L. plantarum |
| | | J-5 | L. plantarum |
| | | J-8 | L. murinus |
| | VI | D-6 | L. sake |
| | | D-8 | L. sake |
| | VII | J-2 | L. murinus |

[a]Based on Apa I, Not I, and Xba I digests
NA - No identifiable species

Example 2

Influence of *Lactobacillus brevis* Strain 1E-1 on the Gastrointestinal Microflora and Performance of Pre-Weaning and Weaning Pigs From the study described in Example 1, it was determined that the intestinal tract of healthy pigs had higher levels of lactobacilli. Genetic analysis of the lactobacilli found in healthy pigs indicated a homogenous population of strains, whereas the lactobacilli populations found in the sick pigs were heterogeneous. The majority of the isolates (59%) were identified as a single genotype (Profile I based on Apa I, Not I and Xba I digests) that was biochemically identified as *L. brevis*. This strain is now referred to as 1E-1 and is the *Lactobacillus* strain used in this example. Lanes 1 and 14 contain a Lambda concatamer as a molecular weight (MW) marker. FIG. 1 shows Apa I digests (left hand lane), Not I digests (middle lane), and Xba I digests (right hand lane) of various strains, including strain 1E-1. All *Lactobacillus* strains with a Profile I based on Apa I, Not I, and Xba I digests are expected to work in the invention.

Materials and Methods

Sows and gilts were blocked by parity and sire and randomly allotted to one of three treatments as they were placed in the farrowing room at 110-112 days of gestation. Litters, starting at birth, received no supplemental milk replacer (control), supplemental milk replacer (18.5% solids, 1.5 lbs/gallon) without 1E-1 (milk), or supplemental milk replacer (18.5% solids, 1.5 lbs/gallon) with 1E-1 (milk plus 1E-1). Pigs received treatments up to the day of weaning. At weaning, pigs within each group were ranked by weight. A phase I diet, fed for the first two weeks post-weaning, contained 3.75% spray-dries plasma and at least 15% lactose. A phase II diet, fed until the completion of the study (28 days), contained 1.0% plasma, 1.5% blood cells, and at least 8% lactose.

The milk replacer system used in this study was an in-line system. The milk replacer was supplied to the pigs ad libitum in a small bowl supplied by a central 30-gallon tank. The tank was equipped with a hydro pump and a pressure regulator that pumped the milk replacer to the pens as needed. A baby pig nipple inside each bowl allowed milk to flow into the bowl only when touched by a pigs nose. This was used to minimize spillage and waste of the milk replacer. The entire system was flushed on a daily basis with hot water to remove spoiled milk or sediment, and fresh milk was prepared using a commercial milk replacer (Merrick's Litter-Gro, Union Center, Wis.).

Whole intestinal tracts were removed from one randomly selected pig per litter at 9-13 days of age and from another at 19-23 days. Tracts were immediately placed in a Whirl-pak® bag containing approximately 200 ml sterile phosphate buffer (0.3 mM $KH_2PO_4$, 1 mM $MgSO_4$, 0.05% cysteine hydrochloride, pH=7.0). Tracts were sent to Agtech Products, Inc. for further analysis, which included enumerating *E. coli* and coliforms, harvesting the bacterial community in the tracts, and community DNA isolation to trace 1E-1 throughout the tracts.

Whole tracts were aseptically cut into pars oesophageal, duodenal, jejunal, and ileal sections, and each section was rinsed with sterile phosphate buffer until all contents were washed out. The section was cut lengthwise to expose the epithelial lining, and the sterile rinse was repeated. The weight of each section was recorded and the section placed in a new Whirl-pak® bag. Sterile phosphate buffer (99 ml) was added to each bag and masticated for 60 seconds. Each sample was plated on VRB (Difco Sparks, Md.) for the enumeration of coliforms and CHROMagar (CHROMagar Paris, France) for the enumeration of *E. coli*. Spiral plating techniques were used at $10^{-1}$ and $10^{-3}$ dilutions on the Autoplate 4000 (Spiral Biotech, Inc., Norwood, Mass.). The remaining liquid was poured into a sterile 250 ml centrifuge bottle and the intestinal scrapings harvested by centrifugation at 8000 rpm for 15 minutes. The supernatant was carefully removed and the pellet was resuspended with 10 ml MRS+10% glycerol. The sample was then transferred to a sterile 15 ml Falcon® tube and stored at −20° C. until DNA isolation.

DNA was isolated from the harvested cells using a High Pure PCR Template Preparation Kit (Roche Diagnostics GmbH, Mannheim, Germany). 1E-1 was then isolated within the community DNA by using PCR on the 16S-23S intergenic spacer region of each sample. Specific primers were used that annealed to conserved regions of the 16S and 23S genes (Tilsala-Timisjarvi, A., and T. Alatossava. 1997 Development of oligonucleotide primers from the 16S-23S rRNA intergenic sequences for identifying different dairy and probiotic lactic acid *Lactobacillus* strain by PCR. Int. J. Food Microbiol. 35: 49-56). PCR was performed following the procedures of Tannock et al. (1999. Identification of *Lactobacillus* isolates from the gastrointestinal tract, silage, and yoghurt by 16S-23S rRNA gene intergenic spacer region sequence comparisons. 65: 4264-4267). PCR mixtures contained 5 µl of 10× polymerase buffer (Boehringer Mannheim), 200 µM each deoxynucleoside triphosphate, 80 µM each primer, 8 µl DNA, and 2.6 U of Expand High Fidelity PCR System (Boehringer Mannheim GmbH, Mannheim, Germany) DNA polymerase in a total volume of 50 µl. The PCR program began with a pre-incubation at 94° C. for 2 min., then 95° C. for 30 s, 55° C. for 30 s, and 72° C. for 30 s. This was repeated for 30 cycles and finished with a 5-min incubation at 72° C. PCR products were then isolated by electrophoresis in a 1% agarose gel and visualized by UV transillumination after being stained in ethidium bromide solution.

Results

Gastrointestinal Microflora:

Pre-Weaning Pigs: There were no significant treatment effects on populations of coliforms within the pars oesophageal, duodenal, and ileal sections of pre-weaning pigs (FIG. 2). The jejunal coliform populations tended to be lower for pigs receiving milk replacer plus 1E-1 compared to control pigs (P<0.12) but were not significantly different when compared to pigs receiving milk replacer alone.

*E. coli* populations enumerated within the pars oesophageal, duodenal, and ileal sections were not significantly different among pre-weaning pigs receiving the three treatments (FIG. 3). However, in the ileal section, there was a trend for lower levels of *E. coli* in the pigs receiving milk plus 1E-1 compared to control pigs and those receiving milk replacer alone. Pigs receiving milk plus 1E-1 had significantly lower jejunal *E. coli* populations compared to control (P<0.02) and milk replacer alone (P<0.05).

Weaning Pigs: The coliform levels within the pars oesophageal, duodenal, and jejunal regions of weaning pigs showed no significance between treatments (FIG. 4). Coliform levels in the ileal region, however, tended to be lower for pigs receiving milk replacer plus 1E-1 when compared to control (P<0.07), but were not significantly different when compared to milk replacer alone.

The *E. coli* levels in the weaning pigs showed some large differences between treatments within the distal regions of the gastrointestinal tract (FIG. 5). There were no significant treatment effects on *E. coli* levels within the pars oesophageal region. In the duodenum, *E. coli* levels tended to be lower for pigs receiving milk replacer plus 1E-1 compared to control (P<.13). Within the jejunal region, pigs receiving milk replacer plus 1E-1 had significantly lower *E. coli* populations compared to the control (P<0.01) and the difference in *E. coli* populations was nearing significance compared to milk replacer alone (P<0.11). The *E. coli* populations in the ileal region showed a significant reduction in *E. coli* levels for pigs receiving milk replacer plus 1E-1 when compared to control (P<0.05) and milk replacer alone (P<0.02).

Overall, the microbial data showed a reduction in coliforms and *E. coli* for pre-weaning and weaning pigs receiving milk replacer plus 1E-1. The most noticeable response was in the distal regions of the gastrointestinal tract compared to the pars oesophageal and duodenal (proximal) regions. The reduction in *E. coli* levels in the pigs was greater than the reduction in the level of coliforms. A greater difference was also observed between treatments in pigs at weaning compared to pre-weaning pigs.

The establishment of strain 1E-1 in the gastrointestinal tract was studied using the 16S-23S intergenic spacer region of 1E-1 (Tannock, G. W., et al. 1999. Identification of *Lactobacillus* isolates from the gastrointestinal tract, silage, and yoghurt by 16S-23S rRNA gene intergenic spacer region sequence comparisons. Appl. Environ. Microbiol. 65: 4264-4267). The intergenic spacer region has been known to be highly variable between lactobacilli. Tannock's results indicated that this was a relatively simple and rapid method by which lactobacilli can be identified without resorting to the use of species-specific primers. The results of this analysis, however, showed identical PCR products between native lactobacilli and strain 1E-1. Even a Cfo I restriction digest did not distinguish between these isolates. Therefore, the use of the 16S-23S intergenic spacer region has not been useful for tracing strain 1E-1 within the gastrointestinal tract.

Performance Data:

Suckling pigs: The suckling performance data is shown below in Table 7. Pigs receiving strain 1E-1 had a significant increase in average daily gain (ADG) from birth to weaning when compared to the control (P=0.07), but not significantly different when compared to pigs fed milk replacer alone. At five days to weaning and ten days to weaning, pigs receiving strain 1E-1 showed a significant increase in ADG when compared to control (P=0.05 and P=0.06, respectively), but not when compared to milk replacer alone. There was no significant difference in weight at weaning for pigs receiving any of the treatments.

TABLE 7

Suckling pig performance data

| Item | Control | Milk | Milk + 1E-1 |
|---|---|---|---|
| ADG, g | | | |
| ADG, birth to 5 d | 128 | 163 | 138 |
| ADG, birth to 10 d | 166 | 186 | 182 |
| ADG, birth to weaning | 192$^b$ | 240$^{a,b}$ | 262$^a$ |
| ADG, 5 d to 10 d | 204 | 208 | 226 |
| ADG, 5 d to weaning | 214$^d$ | 267$^{c,d}$ | 305$^c$ |
| ADG, 10 d to weaning | 221$^f$ | 299$^{e,f}$ | 347$^e$ |
| Weight, kg | | | |
| Litter birth weight | 14.72 | 12.28 | 14.33 |
| Weight at day 5 | 20.39 | 21.74 | 20.74 |
| Weight at day 10 | 28.41 | 21.74 | 28.18 |
| Weight at weaning* | 39.55 | 44.93 | 43.69 |

*Adjusted for age at weaning (average 19.64 d)
$^{a,b}$Means with differing superscripts are significantly different; P = 0.07
$^{c,d}$Means with differing superscripts are significantly different; P = 0.05
$^{e,f}$Means with differing superscripts are significantly different; P = 0.06

Nursery pigs: The nursery pig performance data is shown below in Table 8. Nursery pig performance was monitored to determine the long-term effects of the treatments. In phase 1, the pigs receiving strain 1E-1 had a significant increase in ADG when compared to the pigs receiving milk replacer alone (P<0.05), but were not significantly different compared to pigs fed no milk (control). In phase 2, a significant improvement in the gain:feed ratio was observed for pigs receiving milk alone compared to control pigs (P<0.05), however, there was no significant difference when compared to pigs receiving strain 1E-1. Overall (phase 1 and 2 combined), there was no significant difference for ADG or gain:feed among the treatments. Pigs fed strain 1E-1 had a significantly higher weight at the end of phase 1 compared to pigs receiving milk replacer alone (P=0.07), but the weight was not significantly higher compared to control. At the end of Phase 2, the pigs receiving milk plus strain 1E-1 tended to have a higher weight when compared to control pigs (P=0.11), but the weight was not different compared to the milk replacer alone.

TABLE 8

Nursery pig performance data

| Item | Control | Milk | Milk + 1E-1 |
|---|---|---|---|
| Phase 1 | | | |
| ADG, g | 239$^{a,b}$ | 211$^b$ | 258$^a$ |
| ADFI, g | 228 | 211 | 250 |
| Gain:Feed | 1.109 | 1.031 | 1.139 |
| Phase 2 | | | |
| ADG, g | 466 | 487 | 517 |
| ADFI, g | 633 | 620 | 673 |
| Gain:Feed | 0.736$^b$ | 0.790$^a$ | 0.769$^{a,b}$ |
| Phase 1-2 | | | |
| ADG, g | 352 | 355 | 388 |
| ADFI, g | 431 | 435 | 461 |
| Gain:Feed | 0.823 | 0.828 | 0.850 |
| Weight, kg | | | |
| Initial | 5.21 | 5.50 | 6.31 |
| Phase 1 | 8.51$^{c,d}$ | 8.26$^d$ | 9.88$^c$ |
| Phase 2 | 15.03$^e$ | 15.19$^{e,f}$ | 17.12$^f$ |

$^{a,b}$Means with differing superscripts are significantly different; P < 0.05
$^{c,d}$Means with differing superscripts are significantly different; P = 0.07
$^{e,f}$Means with differing superscripts are significantly different; P = 0.11

Example 3

Influence of *Lactobacillus brevis* Strain 1E-1 on Performance, Intestinal Microflora, and Intestinal Morphology of Pre-Weaning and Weaning Pigs Materials and Methods In each experiment, litters were allotted to two treatments at farrowing: either a control milk supplement, or the control milk supplement containing strain 1E-1. The milk supplement contained 18.5% solids. Treatments were administered throughout the lactation period. After weaning, pigs were grouped 6 pigs per pen.

Coliforms and *E. coli* were enumerated from pars oesophageal, duodenal, jejunal, and ileal regions of the enteric tracts, and gut morphology was assessed from one pig/litter at approximately 10 (pre-weaning) and 22 (weaning) days of age, and after weaning at 28 days of age. Gut morphology was examined to determine villus height and area, crypt depth and the different mucins (neutral, acidic, and sulfuric) produced from enteric goblet cells. Duodenum and ileum tissue samples were taken and sectioned at 4-6 μm. Sections were mounted on polylysine-coated slides and stained with 1) hematoxylin and eosin, 2) alcian blue and periodic acid schiff, and 3) high iron dye. Intestinal microflora populations were determined for pars oesophageal, duodenal, jejunal, and ileal sections. Samples from these regions were processed and each sample was plated. VRB was used for enumeration of coliforms. CHROMagar was used for enumeration of *E. coli*. Spiral plating techniques were used at $10^{-1}$ and $10^{-3}$ dilutions on an Autoplate 4000.

Results and Discussion

Growth performance: Strain 1E-1 supplementation did not affect pig growth performance during the pre- or post-weaning periods. The lack of a performance response with strain 1E-1 supplementation in this Example is likely a consequence of lower coliform and *E. coli* populations in all regions of the gastrointestinal tract from all ages of pigs examined in this experiment. In Example 3, coliform and *E. coli* levels in pre-weaning pigs ranged from 100 to 1000 times lower than coliform and *E. coli* levels in pigs from Example 2. At weaning, coliform and *E. coli* levels in pigs from Example 3 were 1000 times lower in the proximal regions of the gastrointestinal tract and 10 to 100 times lower in the distal regions compared to pigs in Example 2. Although the coliform and *E. coli* levels were reduced by feeding *L. brevis* 1E-1 in Example 3, pig performance was not significantly improved due to decreased pathogenic challenge.

Intestinal Microflora:

Pigs receiving strain 1E-1 had lower jejunal coliform populations pre-weaning (P<0.15) and at weaning (P<0.07) compared to pigs provided only milk supplement, as is shown in FIGS. 6 and 7, respectively. In addition, pigs receiving strain 1E-1 had lower (P<0.001) ileal coliform populations at weaning compared to pigs provided only milk supplement, as is shown in FIG. 7. FIG. 8 shows that pigs receiving strain 1E-1 had lower jejunal *E. coli* populations pre-weaning (P<0.13). FIG. 9 shows that strain 1E-1 reduced *E. coli* populations at weaning in the jejunal (P<0.06) and ileal (P<0.001) compared to pigs provided only milk supplement. In sum, strain 1E-1 was shown to reduce levels of coliforms and *E. coli* within the gastrointestinal tract of pigs, providing a healthier intestinal microflora during the post-weaning period.

Figure 10:
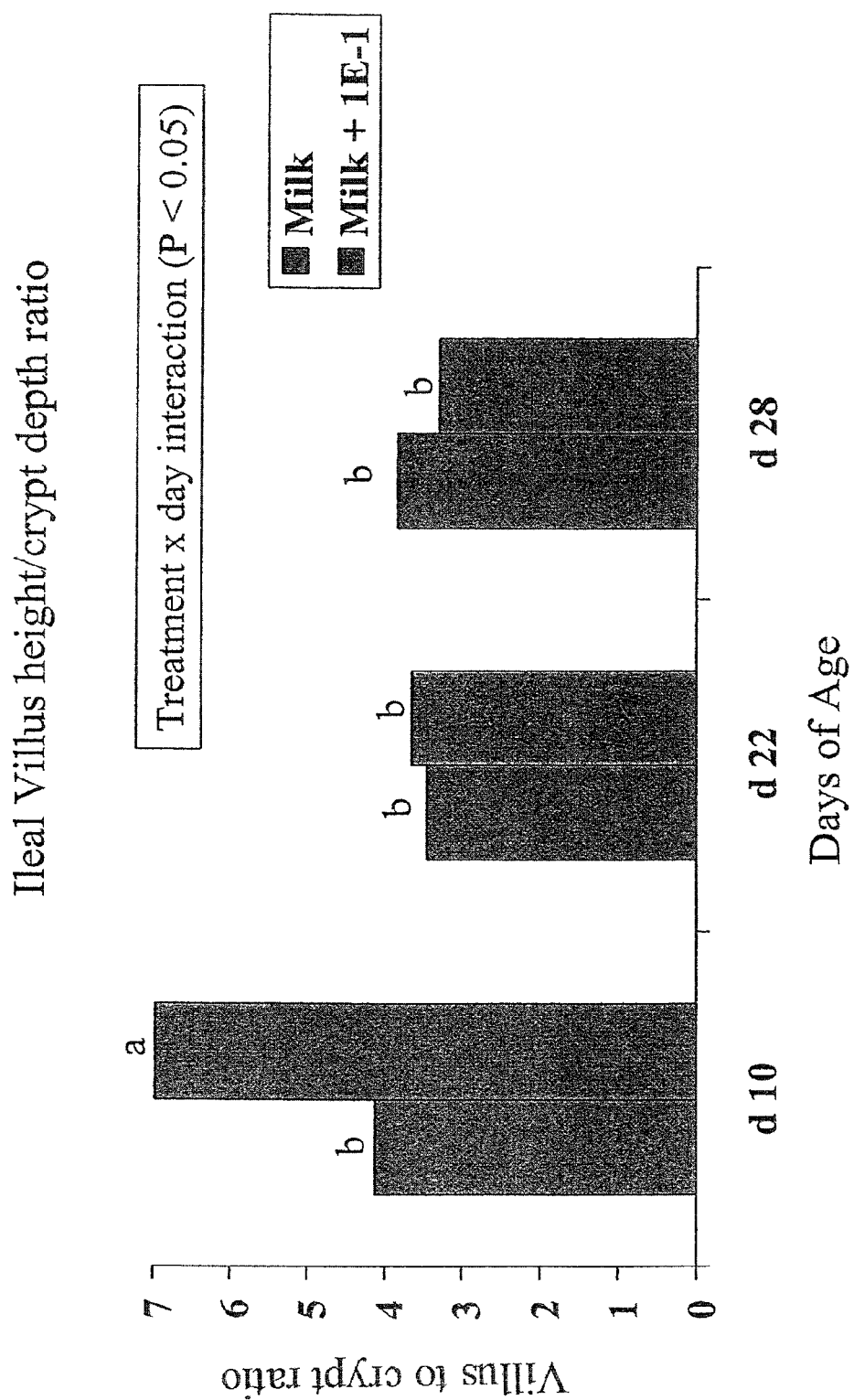
FIG. 10 is a graph showing ileal villus height/crypt depth ratios for pigs at 10, 22, and 28 days.
Figure 11:
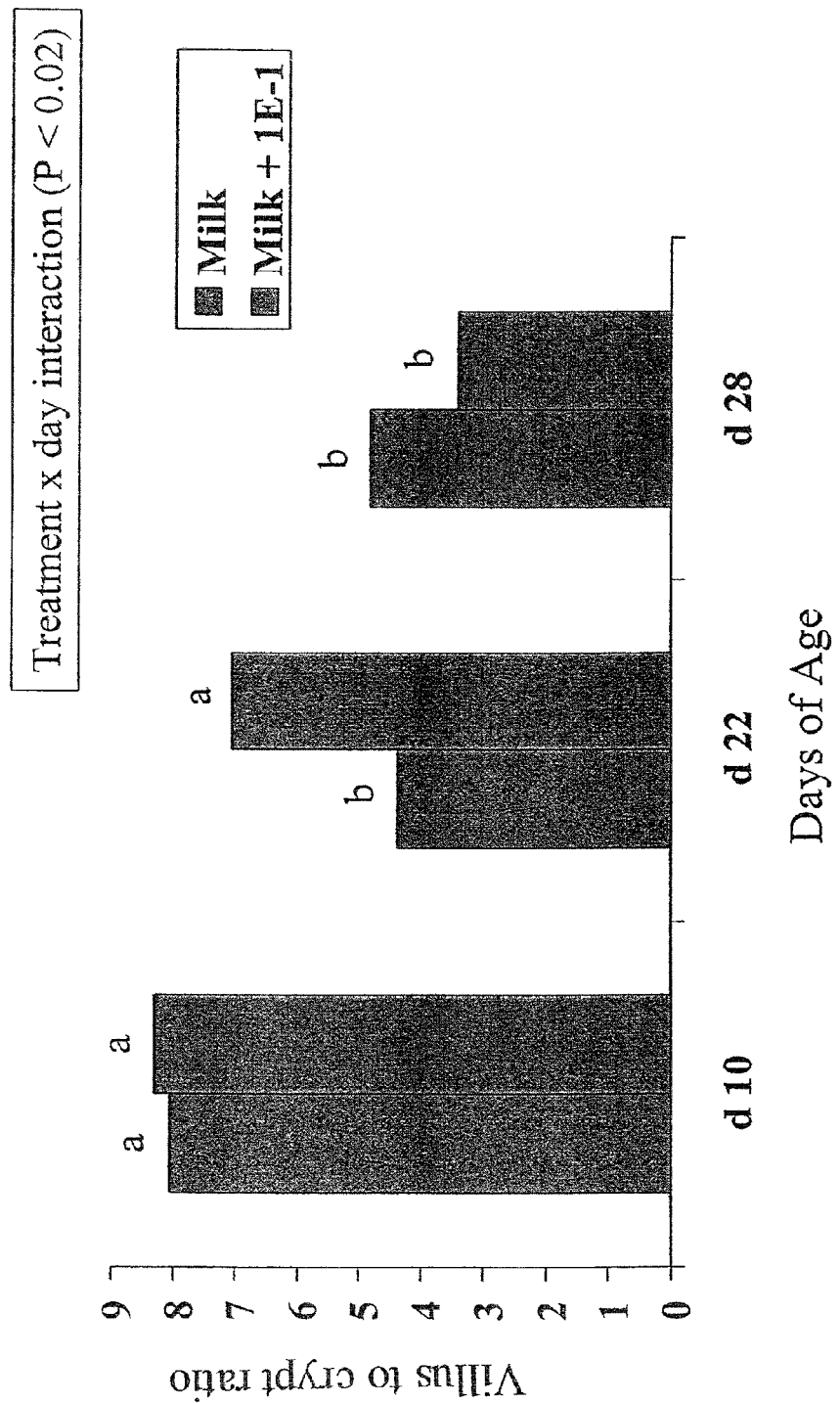
FIG. 11 is a graph showing duodenum villus height/crypt depth ratios for pigs at 10, 22, and 28 days.

Intestinal Morphology: As is shown in FIG. 10, pigs provided strain 1E-1 had greater (P<0.01) ileal villus:crypt ratio at 10 days of age compared to control pigs, although there was no difference at 22 and 28 days of age (interaction, P<0.05). The greater ileal villus:crypt ratio indicates that strain 1E-1 increases the maturation of the distal region of the gut in 10 day old pigs. FIG. 11 shows that pigs provided strain 1E-1 had greater (P<0.01) duodenum villus:crypt ratio at 22 days of age compared to control pigs, although there was no difference at 10 and 28 days of age (interaction, P<0.02).

Figure 12:
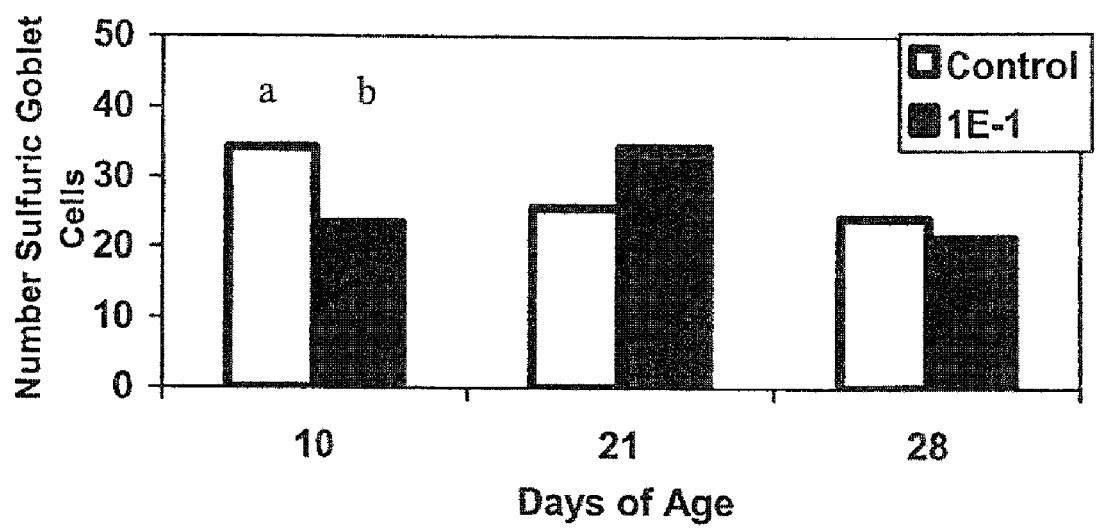
FIG. 12 is a graph showing the number of sulfuric goblet cells in the duodenum of pigs on d 10, 21, and 28 of age (interaction, P<0.06). Means within each day post-weaning with different letter designations differ significantly (P<0.06).

The number of duodenal sulfuric goblet cells was less (P=0.06) when pigs were provided strain 1E-1 compared to control pigs at 10 days of age, although there was no difference at 22 and 28 days of age (interaction, P=0.06; FIG. 12). Sulphomucins are normally absent from the small intestine, but can be produced by crypt goblet cells when the small intestinal mucosa is altered (Specian, R. D. and M. G. Oliver. 1991. Functional biology of intestinal goblet cells. Am. J. Physiol. 260:C183-C193). The decrease in the number of duodenal sulfuric goblet cells by strain 1E-1 in pigs at 10 days of age may be an indication of a healthier gastrointestinal tract. In addition, the lower number of sulfuric goblet cells, combined with the increase in villus:crypt ratio in strain 1E-1-supplemented pigs suggests that strain 1E-1 affords some protection from the intestinal disruption that occurs at weaning.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. The invention is not intended to be limited to the preferred embodiments described above, but rather is intended to be limited only by the claims set out below. Thus, the invention encompasses all alternative embodiments that fall literally or equivalently within the scope of the claims.

What is claimed is:

1. A method of feeding an animal comprising feeding the animal an effective amount of a *Lactobacillus* strain selected from the group consisting of: *L. brevis* strain 1E-1 ATCC Accession No. PTA-6509, a *Lactobacillus* strain having all of the identifying characteristics of the *L. brevis* strain 1E-1 ATCC Accession No. PTA-6509 and combinations thereof.

2. A method of claim 1, wherein the feeding of the *Lactobacillus* strain decreases levels of coliforms within the gastrointestinal tract of an animal.

3. The method of claim 1, wherein the strain fed is *L. brevis* strain 1E-1 ATCC Accession No. PTA-6509.

4. The method of claim 1, wherein the strain is fed with a carrier.

5. The method of claim 1, wherein the strain fed is the *Lactobacillus* strain having all of the identifying characteristics of the *L. brevis* strain 1E-1 ATCC Accession No. PTA-6509.

6. The method of claim 1, wherein the animal is a pig.

7. The method of claim 6, wherein the *Lactobacillus* strain is fed to the pig at least during one of prior to weaning, during weaning, and after weaning.

8. The method of claim 1, wherein the feeding results in about $1\times10^8$ CFU to about $1\times10^{10}$ CFU per day of the *Lactobacillus* strain being delivered to the animal.

9. The method of claim 8, wherein the feeding results in about $5\times10^9$ CFU per day of the *Lactobacillus* strain being delivered to the animal.

10. The method of claim 1, wherein the animal is a pig and wherein the feeding of the *Lactobacillus* strain increases performance of the pig.

11. The method of claim 10, wherein the increase in performance comprises an increase in average daily gain.

12. The method of claim 1, wherein the feeding of the *Lactobacillus* strain improves intestinal morphology of the animal.

13. The method of claim 12, wherein the improvement in intestinal morphology comprises one of (1) an increase in the villus:crypt ratio in the animal and (2) a decrease in the number of sulfuric goblet cells in the animal.

14. The method of claim 1, wherein the feeding of the *Lactobacillus* strain increases a gain:feed ratio in the animal.

* * * * *